US011813299B2

(12) United States Patent
Tsubota et al.

(10) Patent No.: US 11,813,299 B2
(45) Date of Patent: Nov. 14, 2023

(54) COMPOSITION AND FUNCTIONAL FOOD FOR PREVENTING MYOPIA

(71) Applicants: TSUBOTA LABORATORY, INC., Tokyo (JP); ROHTO PHARMACEUTICAL CO., LTD., Osaka (JP)

(72) Inventors: Kazuo Tsubota, Tokyo (JP); Toshihide Kurihara, Tokyo (JP)

(73) Assignees: TSUBOTA LABORATORY, INC., Tokyo (JP); ROHTO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/614,176

(22) PCT Filed: May 15, 2018

(86) PCT No.: PCT/JP2018/018679
§ 371 (c)(1),
(2) Date: Nov. 15, 2019

(87) PCT Pub. No.: WO2018/212152
PCT Pub. Date: Nov. 22, 2018

(65) Prior Publication Data
US 2020/0171112 A1 Jun. 4, 2020

(30) Foreign Application Priority Data

May 15, 2017 (JP) .................... 2017-096792

(51) Int. Cl.
| | | |
|---|---|---|
| *A61K 36/16* | (2006.01) | |
| *A61P 27/10* | (2006.01) | |
| *A61K 9/00* | (2006.01) | |
| *A61K 31/05* | (2006.01) | |
| *A61K 31/202* | (2006.01) | |

(52) U.S. Cl.
CPC ............ *A61K 36/16* (2013.01); *A61K 9/0056* (2013.01); *A61K 31/05* (2013.01); *A61K 31/202* (2013.01); *A61P 27/10* (2018.01)

(58) Field of Classification Search
CPC .................................................. A61K 36/00
USPC ...................................................... 424/725
See application file for complete search history.

(56) References Cited

U.S. PATENT DOCUMENTS

| | | | |
|---|---|---|---|
| 2004/0101578 | A1 | 5/2004 | Kim |
| 2014/0141082 | A1 | 5/2014 | Gao |

FOREIGN PATENT DOCUMENTS

| | | | |
|---|---|---|---|
| CN | 1429563 | A | 7/2003 |
| CN | 1275610 | C | 9/2006 |
| CN | 103039968 | | 4/2013 |
| CN | 106214875 | * | 12/2016 |
| CN | 106578323 | A | 4/2017 |
| JP | 2004151079 | | 5/2004 |
| JP | 2007031426 | * | 2/2007 |
| JP | 2007215465 | | 8/2007 |
| JP | 2010163362 | | 7/2010 |
| JP | 2011162493 | | 8/2011 |

OTHER PUBLICATIONS

Meng et al., Ophthalmological, Axial Length of Myopia: A review of current research, 2011, 225, 127-134.*
International Search Report and Written Opinion issued for Application No. PCT/JP2018/018679, dated Oct. 7, 2018.
With blessings from gardenia, your eyes can be rejuvenated! Health food for eyes "CLGG" appeared. Dec. 12, 2008, pp. 1-3. Search date Jan. 15, 2018, internet: <URL, https://www.value-press.com/pressrelease/32796>, attachments, (ValuePress!), non-official translation (Eyes can be rejuvenated with the benefit of gardenia).
Ishizuka, Fumiya, et al. "Crocetin, a carotenoid derivative, inhibits retinal ischemic damage in mice." European journal of pharmacology 703.1-3 (2013): 1-10.
Ertekin, Mustafa Vecdi, et al. "Effects of oral Ginkgo biloba supplementation on cataract formation and oxidative stress occurring in lenses of rats exposed to total cranium radiotherapy." Japanese journal of ophthalmology 48.5 (2004): 499-502.
Asai, Akira, et al. "Orally administered crocetin and crocins are absorbed into blood plasma as crocetin and its glucuronide conjugates in mice." Journal of agricultural and food chemistry 53.18 (2005): 7302-7306.
Umigai Naofumi, "Gardenia yellow coloring and health-Regarding physiological function of crocetin", New food industry 2013, 55:6, 27-33.
Torii, Hidemasa, et al. "Violet light exposure can be a preventive strategy against myopia progression." EBioMedicine 15 (2017): 210-219.
Schippert, Ruth, et al. "Relative axial myopia in Egr-1 (ZENK) knockout mice." Investigative ophthalmology & visual science 48.1 (2007): 11-17.
Ryo Kawasaki and Kyoko Ohno-Matsui, "Increased prevalence of myopia and pathologic myopia", History of Medicine, vol. 253, No. 2, 2015, 159-161.
Torii, Hidemasa, "Intensity myopia from the viewpoint of aging" Ophthalmology, vol. 58, No. 6, 635-641, 2016.

(Continued)

*Primary Examiner* — Michael V Meller
(74) *Attorney, Agent, or Firm* — Meunier Carlin & Curfman LLC

(57) ABSTRACT

The ophthalmic composition effective for the prevention or treatment of myopia or ocular diseases are provided. In particular, the present invention provides an ophthalmic composition effective in a growing child or a young person in whom myopia develops and progresses, as well as a middle-aged and elderly person in whom age-related ocular diseases such as cataract, glaucoma, retinal detachment, retinopathy, maculopathy, choroidal neovascularization, posterior staphyloma, and optic neuropathy develop, a functional food containing the ophthalmic composition, and a screening method capable of searching for the same. [Solution] The above problem is solved by an ophthalmic composition or functional food product containing at least one component selected from the group consisting of crocetin and its pharmaceutically acceptable salts and ginkgo leaf extract.

7 Claims, 4 Drawing Sheets

(56) References Cited

OTHER PUBLICATIONS

Satoshi Hasebe "Strategies for slowing myopia progression and axial elongation of the eye in schoolchildren", History of Medicine, vol. 245, No. 10, 2013, 880-884.

Lu, Tai Liang, et al. "Axial length and associated factors in children: the Shandong Children Eye Study." Ophthalmologica 235.2 (2016): 78-86.

Tsubota, Kazuo, "If you are still sicking," Your child will be shortsighted if left as it is. ISBN978-4-7993-2041-9 (Publishing company: Discover Twentiwan, date: Feb. 2017). 5 pages.

Wiesel, Torsten N., and Elio Raviola. "Myopia and eye enlargement after neonatal lid fusion in monkeys." Nature 266.5597 (1977): 66-68.

Sherman, S. Murray, T. T. Norton, and V. A. Casagrande. "Myopia in the lid-sutured tree shrew (Tupaia glis)." Brain research 124.1 (1977): 154-157.

Wallman, Josh, Joseph Turkel, and Joseph Trachtman. "Extreme myopia produced by modest change in early visual experience." Science 201.4362 (1978): 1249-1251.

Fischer, Andy J., et al. "Light-and focus-dependent expression of the transcription factor ZENK in the chick retina." Nature neuroscience 2.8 (1999): 706-712.

Machine Translation of Umigai Naofumi. "Gardenia yellow coloring and health-Regarding physiological function of crocetin. New food industry 2013, 55:6, 27-33".

Extended European Search Report issued in EP Application No. 18801518; dated Jan. 20, 2021; 7 pages.

Rusciano et al.; "Neuroprotection in Glaucoma: Old and New Promising Treatments"; Advances in Pharmacological Sciences, vol. 2017; dated Oct. 17, 2017; 20 pages.

Torii, Hidemasa et al. Violet Light Exposure Can Be a Preventative Strategy Against Myopia Progression. EBioMedicine 15 (2017), pp. 210-219, 4 pages.

Schippert, Ruth et al. Relative Axial Myopia in Egr-1 (ZENK) Knockout Mice. Investigative Ophthalmology & Visual Science, Jan. 2007, vol. 48, No. 1, pp. 11-17, 7 pages.

You, Yu et al. Curcumin Inhibited HepG-2 Cell Proliferation through Inducing Egr-1 Gene Expression. Chinese Journal of Cell Biology, 2015, 37(6): 840-845, 6 pages. English Abstract.

* cited by examiner

COMPOSITION AND FUNCTIONAL FOOD FOR PREVENTING MYOPIA

TECHNICAL FIELD

The present invention relates to compositions and functional foods used for the prevention or treatment of myopia or ocular diseases. More particularly, the present invention relates to compositions effective for age groups in which myopia develops or myopia progresses (especially growing children and young people), compositions that is effective also in middle and high-aged people whose risk of eye diseases is increased, or functional foods containing these compositions.

BACKGROUND

There are racial differences in the frequency of myopia. Myopia is more common in Asians, especially in Japanese, with high rate of myopia and high myopia (−5 D or less). In recent years, myopia has been increasing worldwide, and the percentage of children with uncorrected visual acuity of less than 1.0 has been increasing year by year in Japan. It is also known that myopia rapidly progresses in the school age of 7 to 12 years (see Non-Patent Document 1).

Myopia is classified into refractive myopia, accommodative myopia (pseudomyopia), and axial myopia by its pathogenesis, but the progress of myopia in school is mainly axial myopia. Human eye is hyperopic immediately after birth, and the degree of hyperopia decreases due to the ocular axial length elongation during the growth period, and it becomes emmetropic when it enters the school age. Axial elongation after this Emmetropization leads to myopia as it is, and it is not possible to return to the base of the axial length once elongated. Therefore, it is considered that the suppression of the axial elongation in the period from the growth period to the school age is effective for the myopia prevention or treatment (see Non-Patent Document 2). In addition, the axial length elongates not only in the growth phase but also in the adult, and the axial elongation in the adult is said to be a risk factor of various eye diseases, and the high myopia as a result of excessive axial elongation increases the risk of eye diseases such as cataract, glaucoma, retinal detachment, retinopathy, maculopathy, choroidal neovascularization, posterior staphyloma, and optic neuropathy as complications (see Non-Patent Document 2). Thus, inhibition of axial elongation not only results in improved quality of life with myopia prevention but may also lead to prevention of serious ocular diseases leading to blindness.

Various methods have been investigated to suppress this myopic progression (excessive axial elongation). A meta-analysis of the results of previous clinical studies on the inhibition of axial length elongation revealed statistically significant inhibitory effects on axial length in the order of atropine ophthalmic solution, pyrenezepine ophthalmic ointment, orthokeratology, peripheral defocused soft contact lens, and progressive multifocal spectacles. However, there remains a problem to be solved, such as the side effects of atropine ophthalmic solution, the problem of cost burden in orthokeratology and the like, the complexity of measures, and the limited effect of wearing spectacles (see Non-Patent Document 3).

In addition, studies on risk factors for myopia progression (axial elongation) are ongoing, and it is said that age, sex, inheritance, social and living environment, etc. correlate with axial elongation (see Non-Patent Document 4).

In particular, increasing near-work (reading/writing, VDT (Visual Display Terminals) work) and the associated shortage of exposure to sunlight (in particular, 360-400 nm violet light) are attracting attention as risk factors for axial elongation (see Non-Patent Document 5).

Nevertheless, in modern Japanese society, it is impractical to change the main lifestyle of indoors such as study, reading, VDT work, etc., and there is a need for a method of suppressing myopia progression even in a living environment where there is little exposure to violet light due to such near work.

On the other hand, as a study on myopia, an attempt to elucidate the mechanism of ocular axial elongation using animals began in the 1970s, and Wiesel and Raviola demonstrated the association between myopia and axial elongation in rhesus monkey (see Non-Patent Document 6).

Thereafter, myopic animal models have been studied in other animals such as tree shrew, chicken (see Non-Patent Documents 7 and 8).

Many genes involved in the development of axial elongation and myopia have been reported, and EGR-1/ZENK1 is one of them.

Axial elongation and myopia were observed in EGR-1 knockout mice, suggesting that EGR-1 is involved in axial elongation (see Non-Patent Document 9).

However, although axial elongation and progression of myopia were observed in EGR-1 knockout mice, it has not been confirmed whether drugs that enhance the expression of myopia-related genes in a plurality of EGR-1 can actually suppress axial elongation and inhibit myopia progression in in vivo by in vitro.

PRIOR-ART DOCUMENT

Non-Patent Document

[Non-Patent Document 1] History of Medicine, Vol. 253, No. 2, 2015.
Non-Patent Document 2: Ophthalmology, Vol. 58, No. 6, 635-641, 2016.
[Non-Patent Document 3] History of Medicine, Vol. 245, No. 10, 2013.
[Non-Patent Document 4] Ophthalmologica, Vol. 235, 78-86, 2016.
[Non-Patent Document 5] Tsubota, Kazuo, "If you are still sicking," ISBN978-4-7993-2041-9 (Publishing company: Discover Twentiwan, date: February 2017).
[Non-Patent Document 6] Nature, Vol. 266, 66-68, March 1977.
[Non-Patent Document 7] Brain Res, Vol. 124, 154-157, 1977.
[Non-Patent Document 8] Science, Vol. 201, 1249-1251, 1978.
[Non-Patent Document 9] Investigative Ophthalmology & Visual Science, Vol. 48, 11-17, January 2007.
[Non-Patent Document 10] Nat Neurosci, Vo. 2, 705-712, 1999.

SUMMARY OF THE INVENTION

Problems to be Solved the Invention

In general, it is widely known that environmental factors and genetic factors are related to the onset of myopia.

Recently, outdoor activities have been decreasing and indoor activities have been increasing, and mobile phones, game machines, personal computers, liquid crystal televisions, and other devices have become popular, resulting in a living environment in which they are used for a long time in a wide range of age groups, from children to the elderly. The increase in near work leading to myopia and the shortage of violet light exposure due to indoor work are continuing to worsen. Against this background, methods and compositions leading to myopia prevention or screening methods capable of searching for them are strongly demanded. In particular, in view of the fact that the EGR-1 gene is involved in axial elongation, it is possible to effectively prevent myopia and eye diseases if a substance that induces expression of the EGR-1 gene can be screened and the substance can be incorporated into the body by food, medicine, or other methods.

It is an object of the present invention to provide compositions effective for the prevention or treatment of myopia or ocular diseases. In particular, it is an object to provide an ophthalmic composition which is effective in a growing child and a young person in whom myopia develops and progresses, and in a middle-aged and elderly person in whom the risk of ocular diseases such as cataract, glaucoma, retinal detachment, retinopathy, maculopathy, choroidal neovascularization, posterior staphyloma and optic neuropathy is increased, a functional food containing the ophthalmic composition, and a screening method capable of searching for the same.

Means for Solving the Problems

In order to solve the above problems, as a result of various studies by the present inventors, ingredients having effects of enhancing the expression of EGR-1 genes related to ocular axial length elongation were found, and at the same time, ingredients for suppressing ocular axial elongation and preventing myopic progression were found in myopic animal models, and the present inventors were able to complete the present invention. Therefore, the composition according to the present invention can be suitably used for the prevention or treatment of myopia or ocular diseases in which axial elongation is involved. That is, the gist of the present invention is as described below.

[1] An ophthalmic composition comprising at least one ingredient selected from the group consisting of crocetin and its pharmaceutically acceptable salts; and ginkgo leaf extract, for use in the prevention or treatment of myopia or ocular diseases.

[2] The ophthalmic composition according to [1], further comprising crocetin and pharmaceutically acceptable salts thereof, and carotenoids and/or polyphenols other than ginkgo leaf extract.

[3] The ophthalmic composition according to [1] or [2], wherein the myopia is axial myopia.

[4] The ophthalmic composition according to any of [1] to [3], which is for infants in the growth stage.

[5] The ophthalmic composition of any of [1] to [4] where the myopia is high myopia.

[6] The ophthalmic composition according to [1] or [2], wherein the ocular disease is an ocular disease due to aging.

[7] The ophthalmic composition according to [1] or [2], wherein the ocular disease is a complication due to high myopia.

[8] The ophthalmic composition according to [6] or [7], wherein the ocular disease is cataract and posterior segment disease.

[9] The ophthalmic composition according to [8], wherein the posterior segment disease is at least one member selected from the group consisting of glaucoma, retinal detachment, macular hole, foveal sepsis, choroidal neovascularization, posterior staphyloma, myopic macular degeneration, and myopic neuropathy.

[10] The ophthalmic composition according to any of [1] to [9], which is used to suppress ocular axial elongation.

[11] The ophthalmic composition according to any of [1] to [10] for enhancing EGR-1 expressions.

[12] Functional foods for the prevention or treatment of myopia or ocular diseases containing crocetin and its pharmaceutically acceptable salts and at least one ingredient selected from the group consisting of ginkgo leaf extract.

[13] Functional foods product comprising the ophthalmic composition of any of [1] to [11].

[14] A process for screening substances useful for the prevention or treatment of myopia or ocular diseases, characterized in that the presence or absence of an enhancing effect on EGR-1 expression is used as an index.

[15] Ophthalmic compositions comprising a EGR-1 expression enhancer.

[16] The ophthalmic composition according to [15], wherein the EGR-1 expression enhancing agent comprises an antioxidant plant extract.

[17] The ophthalmic composition according to [15] or [16], which is for inhibiting ocular axial elongation.

[18] An ophthalmic composition containing an ocular axial elongation inhibitor.

[19] The ophthalmic composition according to [18], wherein the ocular axial elongation inhibitor comprises an antioxidant plant extract.

[20] The ophthalmic composition according to [15] to [19], which is for the prevention or treatment of myopia or ocular diseases.

[21] An ophthalmic composition containing at least one ingredient selected from the group consisting of crocetin and its pharmaceutically acceptable salts, and ginkgo leaf extract, for near and/or indoor workers.

[22] The ophthalmic composition of [21], which is for childrens use.

Advantageous Effect of the Invention

According to the present invention, there can be provided an ophthalmic composition effective for prevention or treatment of myopia or ocular diseases, a functional food containing the same, and a screening method capable of searching for the same. In particular, the ophthalmic composition of the present invention is suitably used for the prevention or treatment of symptoms and diseases in growing children and young people in whom myopia tends to develop and progress, and in middle-aged and elderly people in whom the risk of ocular diseases, such as cataract, glaucoma, retinal detachment, retinopathy, maculopathy, choroidal neovascularization, posterior staphyloma, and optic neuropathy, is increased.

The present screening methods are also useful for developing ophthalmic compositions, functional foods, and the like capable of obtaining substances capable of improving the effects of inhibiting ocular axial elongation or EGR-1 expression and effectively improving myopia or ocular diseases.

EXAMPLES FOR CARRYING OUT THE INVENTION

Figure 1:
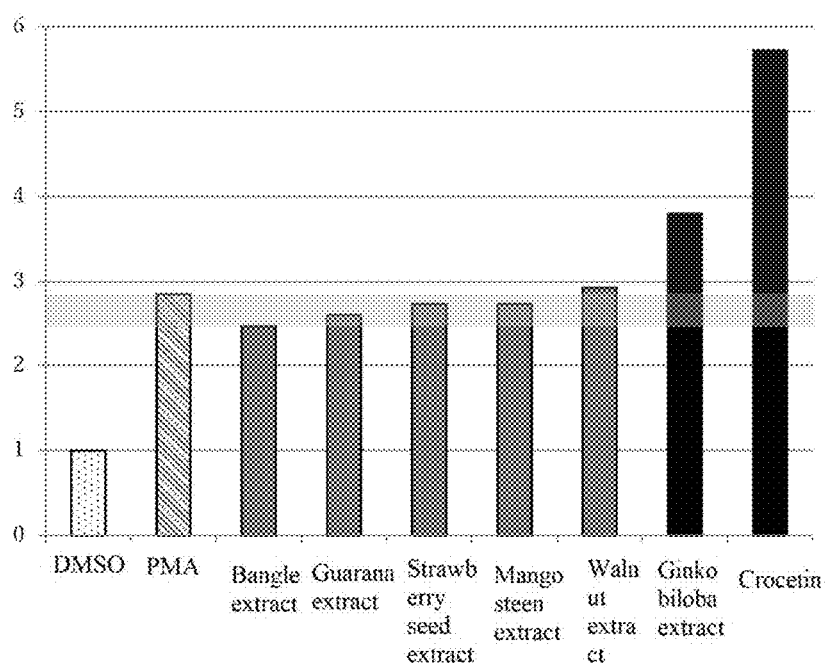
FIG. 1 is a graphical representation of the effects of ingredients included in the inventive ophthalmic compositions on EGR-1 gene expression.

Ophthalmic compositions, functional foods and screening methods according to the present invention are described in detail below. The present invention is not limited to the following embodiments as far as the gist thereof is included, but includes modifications and applications.

Ophthalmic Composition/First Embodiment

A first embodiment of the ophthalmic composition of the present invention contains an antioxidant plant extract or a component derived therefrom, preferably carotenoids, polyphenols. These components have the function of regulating the expression of genes (EGR-1) involved in axial extension that can cause axial myopia and various ocular diseases. Therefore, the ophthalmic composition containing these components has an effect of maintaining visual acuity and is particularly effective for the age group (children in the growth stage, young group, etc.) in which myopia tends to develop and progress. It is also effective against ocular diseases such as cataract, glaucoma, retinal detachment, retinopathy, maculopathy, choroidal neovascularization, posterior staphyloma, and optic neuropathy, which are thought to be caused by axial elongation. The ophthalmic composition may contain other ingredients in addition to the antioxidant plant extract which is an essential ingredient or ingredients derived therefrom so long as the effect of the present invention is not impaired. Hereinafter, the components contained in the ophthalmic composition of the present invention will be described in detail.

The carotenoids contained in the ophthalmic composition of the present invention may include crocetin, a pharmaceutically acceptable salt of crocetin, gardenia extract, gardenia pigment, saffron extract, germinated broccoli extract, broccoli sprout extract, paplica extract, beta-carotene, lutein, zeaxanthin, astaxanthin, marigold extract, red paplica, paplica pigment, western ginseng extract, pepper extract, eucommia leaf extract, safflower extract, apocynum extract, and the like.

Polyphenols, like carotenoids, have antioxidant properties and are collectively referred to as compounds with bitter, astringent, and pigmentary components contained in plants. Polyphenols contained in the ophthalmic compositions of the present invention include ginkgo leaf extract, mangosteen extract, strawberry seed extract, walnut polyphenol, guarana extract, Java ginger extract, nobiletin, blueberry leaf extract, melinjo extract, grape resveratrol, vaccinium extract, gunetin C, ε-viniferin, resveratrol, grape seed extract, black soybean seed coat polyphenol, black bean seed coat polyphenol, cassis extract, curcumin, white curcuminoid, polymethoxyflavonoid (PMF), dihydroquercetin, silybum extract, silymarin, silibinin, aG hesperidin, hesperidin, methyl hesperidin, orange-derived lutinoside, hesperetin, pycnogenol, oligonol, linum seed lignane, parsley extract, maquiberry extract, kiwi seed extract, perilla seed extract, perilla leaf extract, perilla herb, aroma extract, lonicera extract, cyanidin-3-glucoside, quercus extract, euterpe extract, myrciaria extract, malon polyphenol, soy isoflavone, citrus fruit extract, seaweed polyphenol, wine pumice extract, olive fruit extract, sudachi peel extract, lotus root extract, turmeric extract, echinacea, load leaf extract, cistanche tubulosa, guava leaf extract, hoe leaf extract, safflower extract, corn silk extract, salacia extract, plantago herb extract, quickthorn extract, dried orange peel extract, panax notoginseng extract, sweet tea extract, sour orange extract, houttuynia extract, yacon extract, lafuma extract, green tea extract, and the like may be mentioned. Note that the names in parentheses are aliases.

As the carotenoids and polyphenols, those having an excellent action of suppressing the axial length elongation and exhibiting additional characteristics such as maintainability, stability, and the like are preferable.

In view of the above, for carotenoids, crocetin, a pharmaceutically acceptable salt of crocetin, a pharmaceutically acceptable salt of crocetin, gardenia extract, gardenia pigment, saffron extract, beta-carotene, lutein, zeaxanthin, astaxanthin, marigold extract, red paplica, paplica pigment, safflower extract, apocynum extract are preferred, and crocetin, a pharmaceutically acceptable salt of crocetin, gardenia extract, gardenia pigment, and saffron extract are more preferred, and crocetin or a pharmaceutically acceptable salt of crocetin are more preferred.

"From the above point of view, in the polyphenols, ginkgo leaf extract, mangosteen extract, strawberry seed extract, walnut polyphenol, guarana extract, java ginger extract, nobiletin, blueberry leaf extract, cassis extract, curcumin, white curcuminoid, parsley extract, japanese cypress berry extract, polymethoxyflavonoid (PMF) are preferable, and ginkgo leaf extract, mangosteen extract, strawberry seed extract, walnut polyphenol, guarana extract, java ginger extract are more preferable, and ginkgo leaf extract is more preferable.

In this specification, "myopia" is axial myopia, and refers to myopia caused by axial elongation. Axial elongation can be detected using accommodative paralytics or mydriatics. In other words, myopia here is caused by a shift in the focus of the naked eye except for the portion that is focused by the lens or ciliary body, and is different from myopia that is restored when temporary eye fatigue (fatigue of the ciliary muscle) is removed, such as accommodative myopia (pseudomyopia). Thus, myopia as used herein can also be defined as "reduced visual function," "reduced visual acuity," "reduced distance vision," "reduced distance vision," "reduced basic eye performance," "reduced natural vision," or "defocus."

More specifically, myopia is a symptom in which an image is formed in front of the retina and the eye is out of focus on a distant object and is caused by an increase in the axial length of the eye. Such myopia is irreversible and does not return to normal, unlike symptoms caused by temporary paralysis of the ciliary body due to eye fatigue (asthenopia), accommodative spasm, accommodative tension, etc. (hereinafter referred to as "accommodative dysfunction" for convenience). Accommodative dysfunction, conventionally called pseudomyopia or accommodative tension myopia, is a dysfunction based on transient accommodative spasm or accommodative tension and is not myopia. Accommodative dysfunction does not change to myopia because the symptoms are neglected, but it is a symptom that improves by resting the eyes and by stopping the convulsion of the ciliary body with ophthalmic solution to relieve the tension of the lens. However, these treatments cannot cure myopia. For example, in general, myopia recovery and the like are advertised for accommodative dysfunction and not for myopia. Therefore, if accommodative dysfunction is present in combination with myopia, resting the eyes will only restore accommodative dysfunction.

Accordingly, the present invention is directed to the prevention or treatment of ocular diseases caused by myopia or mainly by myopia, and is characterized in that it is inherently and fundamentally different from that for improving accommodative dysfunction caused by, for example, ocular fatigue, accommodative cramping, accommodative tone, etc., which temporarily paralyzes the ciliary body and worsens the movement of the lens.

Also, in the present specification, the term "ocular disease" refers to a disease related to the eye, in particular, an ocular disease caused by myopia, and specifically, cataract or posterior segment ocular disease can be cited. As used herein, "posterior ocular disease" refers to a disease in the vitreous, retina, choroid, sclera, or optic nerve, and specifically includes glaucoma, retinal detachment, macular foramen, fovea fovea, choroidal neovascularization, posterior staphyloma, myopic macular degeneration, and myopic neuropathy. However, the present embodiment is not limited to these definitions, and is broadly applicable to symptoms, diseases, and the like related to axial extension.

Prevention or treatment of myopia or ocular disease referred to herein means suppression of myopia progression (axial elongation), suppression of abnormal axial elongation different from normal axial elongation (normal emmetropization) from infancy to school childhood, and prevention and treatment of complications that occur concomitantly therewith. That is, the prevention or treatment of myopia or ocular disease referred to herein can be defined not only as the prevention or treatment of myopia referred to in the preceding paragraph (paragraph 0022), but also as "normalization of refractive changes or corneal curvature radius changes due to axial elongation", "healthy eye growth support", "support of the eye during growth", "maintenance of visual function", or "anti-aging of the eye".

The following is a detailed description of crocetin, a pharmaceutically acceptable salt of crocetin, ginkgo leaf extract, which the first embodiment of the ophthalmic composition of the present invention particularly preferably contains.

Crosetin is a group of natural pigments and is one of the components classified as carotenoids. Crosetin is a potent antioxidant and can be extracted to high purities from the fruits of gardenia (*Gardenia augusta* MERRIL var., *grandiflora* HORT., *Gardenia jasminoides* ELLIS) and the stigma of saffron (*Crocus sativus*).

Crocetin is usually obtained by hydrolyzing a yellow pigment of the carotenoid series, crocin (a digentiobiose ester of crocetin). Crocinis included in the fruit of gardenia, the stigma of saffron, etc., but crocinis preferably used as an industrial material for obtaining crocetin.

The method of extracting crocinfrom the plant base is not particularly limited, and, for example, a known method such as extracting water or alcohol (e.g., methanol, ethanol, etc.) from crushed gardenia dried fruit or a mixture thereof is used. The extraction conditions are preferably from 0 to 50° C. for 1 to 18 hours and more preferably from 30 to 40° C. for 2 to 4 hours, for example, when a water/alcohol mixture is used. The extraction operation is usually repeated several times.

Industrially, it is preferred that the hydrolysis of crocin is by alkali hydrolysis. The hydrolysis may also be carried out under stirring and/or heating. It is preferable to carry out the hydrolysis at 20 to 70° C. under stirring, and it is carried out at 40 to 60° C. for 1 to 24 hours, preferably 3 to 5 hours.

When the hydrolysis of crocinis hydrolysis by alkaline, generally, after the hydrolysis is completed, crocetin can be precipitated by adding an appropriate amount of an aqueous solution of an inorganic acid such as hydrochloric acid, sulfuric acid, phosphoric acid, or the like, or an organic acid such as citric acid, or the like, to the reaction solution, and setting the reaction solution to pH4.0 or less, preferably pH1.0 to 3.0. Thereafter, the mixed solution in which crocetin is precipitated is centrifuged or filtered, whereby crocetin can be recovered as a paste-like solid.

Since the obtained crocetin usually has impurities derived from acid, neutralized salt and raw material attached to the surface of the solid matter, washing treatment is performed for the purpose of removing the impurities.

The treatment may be performed by a known method such as, for example, washing the paste-like solid material with a sufficient amount of water.

The washed solids may then be dried, e.g., using a shelf-type air dryer, vacuum dryer, or the like, preferably at a temperature not exceeding about 50° C. under an atmosphere of nitrogen gas, to remove water remaining in the solids.

Crocetin is preferred in terms of less imperfections if it is more than 50% pure but it is not limited to pure if it can even obtain effective chromatin content.

The purity of crocetin can be calculated on the basis of the color value of the pure crocetin.

The color value can be calculated by referring to the "Voluntary Standard for Food Additives Other than Chemical Synthetic Products (Second Edition)", Japan Food Additives Society, Editor, "*Gardenia* yellow pigment".

Crocetin may be obtained by hydrolyzing crocin contained in natural products such as plants as described above or may be chemically synthesized. Also, those contained in natural products such as gardenia fruit, gardenia extract, and saffron extract may be used. From the standpoint of safety and purity, it is more desirable to obtain crocetin from gardenia yellow pigment (example of food labeling).

Pharmacologically acceptable salts of crocetin include, for example, alkali metal salts such as sodium, potassium, and the like; alkaline earth metal salts such as magnesium, calcium, and the like; salts of pharmaceutically acceptable organic amino compounds such as pyridine, dimethylamine, diethylamine, ethanolamine, and the like.

As a commercially available crocetin preparation, for example, Crovit (trademark) manufactured by Riken Vitamin Co., Ltd. can be exemplified. "Crovit P" (trademark) is a powder with a crocetin content of 75% or more, and "Crovit 2. 5WD" (trademark) is a water-dispersible product with a crocetin content of 2.5% or more.

The method for qualitative and quantitative determination of crocetin or its pharmaceutically acceptable salts in the inventive ophthalmic compositions is not particularly limited as long as it is a scientifically reasonable method. For example, samples can be separated by high performance liquid chromatography using ODS columns and a gradient mobile phase (TFA aqueous solution→TFA aqueous-methanol solution), and the test substance can be qualitatively and quantitatively determined by a photodiode array detector using all-trans-crocetin, 13-cis-crocetin, or the like as a reference material.

Ginkgo leaf extract is a plant extract based on terpene lactones typified by many flavonoids such as quercetin, kenferol, and proanthocyanidin and gincholide, which is effective in improving blood flow, and can be extracted from dried ginkgo leaves (*Ginkgo biloba*. L.) by conventional methods.

Examples of commercially available ginkgo leaf extract include "Dried ginkgo leaf extract" (manufactured by Indena Japan Co., Ltd.), "Ginkgo extract BG-50" (manufactured by Kanei Kogyo Co., Ltd.), "Ginkgo extract-FM" (manufactured by Tama Biochemistry Co., Ltd.), "Ginkgo leaf extract-F" (manufactured by Tama Biochemistry Co., Ltd.), and "Ginkgo leaf extract-C" (manufactured by Maruzen Pharmaceutical Co., Ltd.).

The content of the antioxidant plant extract such as crocetin, a pharmaceutically acceptable salt of crocetin, ginkgo leaf extract, or the like, or components derived therefrom, which is contained in the ophthalmic composition of the present invention, is not particularly limited, but the amount per day is preferably 0.001 to 5000 mg/day, preferably 0.01 to 1000 mg/day, and more preferably 0.01 to 500 mg/day.

The inventive ophthalmic compositions contain the above-mentioned components having the effects of enhancing the expression of EGR-1 genes related to inhibition of ocular axial elongation and are therefore suitably used for enhancing EGR-1 expression and for inhibiting axial elongation.

In addition, the ophthalmic compositions of the present invention are suitably used for the prevention or treatment of myopia (in particular axial myopia) or ocular diseases involving axial elongation (in particular posterior ocular diseases, which are at least one selected from the group consisting of glaucoma, retinal detachment, macular foramen, foveal sepsis, choroidal neovascularization, posterior staphyloma, myopic macular degeneration, and myopic neuropathy). Pharmaceuticals and foods which are preferred embodiments of such ophthalmic compositions are described in detail below.

<Medicine>

When the ophthalmic composition of the present invention is pharmaceutical, a pharmaceutically acceptable excipient or the like may be added to the pharmaceutical formulation. The medicine of the present invention can be, but is not limited to, eye drops, oral preparations (solid preparations such as tablets, capsules, granules, fine granules, powders, chewables, lozenges, liquid preparations such as solutions, syrups, and the like), injection preparations, and the like, which can be used for the prevention or treatment of myopia or ocular diseases.

Among these, an ophthalmic solution and an oral agent are preferable from the viewpoint of easily achieving the effect of the present invention. The ophthalmic composition of the present invention may contain other additives other than those described above, depending on the respective properties, applications, and the like.

When the ophthalmic composition of the present invention is used as a medicament, the study symptoms and diseases are not particularly limited as long as they are considered to be one of the causes of axial elongation, but myopia and ocular diseases are preferable. As myopia, axial myopia is preferable, and in particular, axial myopia is more preferable in a growing child or a young person who is likely to develop or progress axial myopia.

Ophthalmic diseases are preferably cataracts, glaucoma, retinal detachment, retinopathy, maculopathy, choroidal neovascularization, posterior staphyloma and optic neuropathy, particularly cataracts, glaucoma, retinal detachment, macular foramen, fovea fovea, choroidal neovascularization, posterior staphyloma, myopic macular degeneration and myopic neuropathy.

When the ophthalmic composition of the present invention is used as a medicament, the subject is a person in need of prophylaxis or treatment of myopia or ocular diseases, in particular a growing child or young group in which the onset or progression of myopia, especially axial myopia, is likely to occur, in particular a child mainly under the age of 20 and a young group in the age of 20 to 30, preferably between 2 and 15, more preferably between 6 and 12 years of age. It is also suitable for use in middle-aged and elderly patients with increased risk of age-related eye diseases such as cataract, glaucoma, retinal detachment, macular hole, foveal segregation, retinal edema, diabetic retinopathy, retinal pigment degeneration, macular edema, diabetic macular disease, myopic macular degeneration, age-related macular degeneration, and myopic neuropathy, in accordance with their symptoms.

When the ophthalmic composition of the present invention is used for near-work workers and/or indoor workers, there is no particular limitation as long as the person has a risk factor for the extension of the eye axis, but the subject is mainly a person who has a large number of near-work indoors or a person who has little exposure to violet light (visible light of 360 to 400 nm) outdoors. In particular, children and schoolchildren who spend a relatively long time on study, reading, personal computer, television, and video games are preferred, and elderly people who tend to have fewer outdoor activities are also preferred.

<Eye-Drops>

When the ophthalmic composition of the present invention is used as an ophthalmic solution, the solubility and stability of at least an antioxidant plant extract such as crocetin or a pharmaceutically acceptable salt thereof in water are considered, and the composition is selected from aqueous ophthalmic solutions, dissolved ophthalmic solutions at the time of use, suspensions, oily ophthalmic solutions, ophthalmic ointments, and the like. For example, because crocetin is water-soluble in carotenoids, which combine a water-miscible structure and an oil-miscible structure, the dosage forms of the ophthalmic compositions of the present invention may generally be aqueous eye drops or suspensions.

The ophthalmic solution may contain other active ingredients (pharmacologically active ingredient, biologically active ingredient, etc.) in addition to the above ingredients. The type of such a component is not particularly limited, and examples thereof include a decongestant component, an ophthalmic muscle regulator component, an anti-inflammatory drug component, an astringent component, an antihistamine drug component, an antiallergic drug component, a vitamin, an amino acid, an antimicrobial drug component, a saccharide, a polymer compound or a derivative thereof, cellulose or a derivative thereof, a local anesthetic component, a glaucoma treatment component other than the above component, a cataract treatment component other than the above component, and the like.

In the eye drops, various components and additives may be appropriately selected according to conventional methods depending on the use and form thereof, and one or more of them may be used in combination to contain the eye drops, to the extent that the effect of the present invention is not impaired. These ingredients or additives may include, for example, various additives such as carriers, perfumes or cooling agents, preservatives, fungicides or antimicrobial agents, pH adjusting agents, chelating agents, stabilizing agents, isotonic agents, buffering agents, thickening agents, and the like, which are commonly used in the preparation of liquids and the like.

The following are illustrative, but not limiting, of typical ingredients used in eye drops.

Examples of the carrier include aqueous solvents such as water and water-containing ethanol. When the various components are hardly soluble in an aqueous solvent, a solubilizing agent may be used. Examples of the solubilizing agent include polyoxyethylene hardened castor oil, polyoxyl 40 stearate, povidone, polysorbate 80, and the like.

Perfumes or cooling agents include, for example, terpenes (e.g., anethol, eugenol, camphor, geraniol, cineol, borneol, menthol, limonene, rheumatoid arthritis, etc., which may be in the d, l or dl forms), essential oils (e.g., geese oil, coolmint oil, keihi oil, spearmint oil, hacker water, peppermint oil, bergamot oil, eucalyptus oil, rose oil, etc.), and the like.

Preservatives, fungicides or antimicrobials include, for example, polydronium chloride, alkyldiaminoethylglycine hydrochloride, sodium benzoate, ethanol, benzalkonium chloride, benzethonium chloride, chlorhexidine gluconate, chlorobutanol, sorbic acid, potassium sorbate, sodium dehydroacetate, methyl parahydroxybenzoate, ethyl parahydroxybenzoate, propyl parahydroxybenzoate, butyl parahydroxybenzoate, oxyquinoline sulfate, phenetyl alcohol, benzyl alcohol, biguanide compounds (specifically, polyhexamethylene biguanide), Growkill (trademark, manufactured by Rhodia), and the like.

Examples of the pH adjusting agent include hydrochloric acid, sodium hydroxide, potassium hydroxide, calcium hydroxide, magnesium hydroxide, triethanolamine, monoethanolamine, diisopropanolamine, sulfuric acid, phosphoric acid, and the like.

Examples of the chelating agent include ascorbic acid, tetrasodium edetate, sodium edetate, citric acid, and the like.

Examples of the stabilizing agent include sodium edetate hydrate, povidone, polysorbate 80, dibutyl hydroxytoluene, trometamol, sodium formaldehyde sulfoxylate (long gallite), tocopherol, sodium pyrosulfite, monoethanolamine, aluminum monostearate, glycerin monostearate, and the like.

Examples of isotonic agents include potassium chloride, sodium chloride, concentrated glycerin, glucose, D-mannitol, and the like.

Examples of the buffer include sodium citrate hydrate, sodium acetate hydrate, sodium bicarbonate, trometamol, boric acid, borax, sodium hydrogen phosphate hydrate, sodium dihydrogen phosphate, and the like.

Examples of the viscous additives include carboxyvinyl polymer, povidone, polyvinyl alcohol (partially saponified), hydroxyethylcellulose, hypromellose, methylcellulose, glycerin, and the like.

The ophthalmic solution of the present invention preferably contains 0.001 to 1% by weight of an antioxidant plant extract such as crocetin or a pharmaceutically acceptable salt thereof or a component derived therefrom, and more preferably contains 0.01 to 0.1% by weight. In addition, other additives can be formulated in anticipation of the effect of the present invention or within a range that does not inhibit the effect of the present invention. The content is not particularly limited, but it is preferable that the content in the composition is about 0.001 to 1 mass %.

The pH of the ophthalmic solution may be 3 to 10, preferably 4 to 9, and more preferably 5 to 8.5 from the standpoint of feeling of use.

As the container for filling the ophthalmic solution of the present invention, a known ophthalmic solution container can be used without limitation. As the eye dropping container, it is possible to use a shape in which an eye dropping agent can be dripped onto an eye, for example, a shape in which a nozzle is provided, and a container opening is provided at the tip of the nozzle. The eyedropper containing the eyedropper of the present invention may be any of a structure in which a nozzle formed separately from that of the container is mounted, and a structure in which a nozzle portion (a popping of liquid) and a container body are integrated (e.g., one-use-up type eyedropper, etc.).

The container containing the ophthalmic solution of the present invention is usually made of plastic. The constituent material of the plastic container is not particularly limited, and for example, any one of polyethylene terephthalate, polyarylate, polyethylene naphthalate, polycarbonate, polyethylene, polypropylene, and polyimide, a copolymer hereof, or a mixture of two or more thereof can be given. In particular, polyethylene terephthalate, polyarylate, polyethylene naphthalate, copolymers thereof, or mixtures of two or more thereof are preferable from the viewpoint that the effect of the present invention can be easily exhibited by the addition or reduction of extrusion or the like.

The ophthalmic solution of the present invention may be filled in a transparent container made of such a material as a main material (a container having transparency enough to observe a foreign substance) or may be filled in a container which is shielded from light. The light shielding may be performed, for example, by adding a coloring agent to the transparent container material, or by covering the container with a shrink film, an outer box, or the like, the container may be shielded from light. The capacity of the container is preferably about 0.5 to 50 mL, and more preferably about 3 to 20 mL, in order to make the effect of the present invention easier to be exhibited by the addition or reduction of extrusion or the like.

In addition, the nozzle provided in the container containing the eye drops of the present invention is not particularly limited in its structure or constituent material. The structure of the nozzle may be any structure as long as it is generally employed as the nozzle of the eye drop container, and the constituent material of the nozzle is, for example, the same as the constituent material of the plastic container. From the viewpoint of further improving the drainage of the ophthalmic solution of the present invention and suppressing the variation of the dropping amount, a nozzle containing polyethylene or polypropylene as a constituent material is suitable. Examples of the type of polyethylene include high density polyethylene, low density polyethylene, and the like, and among them, nozzles containing low density polyethylene as a constituent material are suitable.

<Manufacturing Method of Eye Drops>

The ophthalmic solution of the present invention can be prepared by methods commonly used and known to those skilled in the art. For example, after each component is dispersed in a carrier such as water, a solubilizing agent may be added if necessary, warmed as necessary, homogenized, dissolved or emulsified using a homogenizer or the like, and the pH may be adjusted with a pH adjusting agent. As a method of sterilizing the preparation, a method such as autoclave sterilization, filtration sterilization, or the like can be selected.

<Method of Using>

The dosage and administration of the ophthalmic solution of the present invention varies depending on the symptoms, age, and the like of the patient, but in general, about 1 to 2 drops may be instilled at a time, about 1 to 6 times a day.

<Oral Preparation: Solid Preparation>

The ophthalmic compositions of the present invention can be, for example, solid formulations such as tablets, capsules, granules, powders, and the like. Oral preparations have the advantage that they are excellent in portability and can be easily taken in a certain amount from the mouth. The shape, weight, size, color, and the like of the oral agent are designed in consideration of ease of handling and easy ingestion. The solid preparation may contain one or more of various components and additives selected as appropriate in accordance with conventional methods according to its use and form. As these components or additives, excipients, lubricants, binders, disintegrating agents and the like can be blended in addition to components such as the above-mentioned antioxidant plant extract such as crocetin or a pharmaceutically acceptable salt thereof or components derived therefrom, carotenoids, polyphenols and the like. If necessary, additives such as preservatives, antioxidants, colorants, sweeteners, and the like can be used. The following are illustrative, but not limiting, of typical ingredients used in solid formulations.

Excipients include, for example, sugar alcohols such as D-sorbitol, mannitol, xylitol, sugars such as glucose, sucrose, lactose, fructose, etc., crystalline cellulose, carmellose sodium, croscarmellose sodium, calcium hydrogen phosphate, wheat starch, rice starch, corn starch, valley starch, dextrin, β-cyclodextrin, light anhydrous silicic acid, titanium oxide, magnesium aluminate metasilicate, talc, kaolin, olive oil, etc.

Examples of the binder include cellulose derivatives such as methylcellulose, ethylcellulose, hydroxypropylcellulose, hydroxypropylmethylcellulose, and the like, polyvinylpyrrolidone, polyvinyl alcohol, acrylic acid polymer, gelatin, gum arabic, pullulan, alphalized starch, agar, tragant, sodium alginate, propylene glycol ester alginate, and the like.

Disintegrants include, for example, starch, low substitution hydroxypropyl cellulose, carboxymethylcellulose calcium, croscarmellose sodium, hydroxypropyl starch, partially alphalized starch, and the like.

Examples of the lubricant include stearic acid, magnesium stearate, calcium stearate, polyoxyl stearate, cetanol, talc, hardened oil, sucrose fatty acid ester, dimethylpolysiloxane, beeswax, salamander wax, and the like.

These additives can be incorporated within a range that does not inhibit the effect of the present invention.

<Method for Producing Oral Drugs: Solid Formulations>

When the ophthalmic composition of the present invention is used as a solid formulation, it can be prepared by methods commonly used and known to those skilled in the art. For example, there are exemplified a method of pulverizing and granulating an extruded granulated product formed by kneading a composition and passing it through a screen, a method of adding kneading water to the composition and agitating granulation formed by a vertical granulator, followed by pulverizing and sieving using a corn ill, and a method of compressing the formulation composition by a roller compactor and then pulverizing and sieving with a roll granulator, and a method of fluidized bed drying after agitating and granulating the formulation composition. Further, for example, in the case of manufacturing by direct compression, the composition may be mixed and then directly put into a tablet press to compress the tablet.

<Oral: Liquid Formulations>

The ophthalmic compositions of the present invention may also be in liquid form, for example, as syrups, drinks, and the like, in addition to the above-mentioned components, a solvent, a dissolution aid, a suspending agent, an isotonic agent, a buffering agent, an analgesic agent, and the like can be added to the liquid formulation. Additives such as preservatives, antioxidants, colorant sweeteners and the like may also be used as necessary. These additives can be incorporated within a range that does not inhibit the effect of the present invention.

Examples of the solvent include water, alcohol, propylene glycol, macrogol, sesame oil, corn oil, and the like.

Examples of dissolution aids include polyethylene glycol, propylene glycol, D-mannitol, benzyl benzoate, ethanol, trisaminomethane, cholesterol, triethanolamine, sodium carbonate, sodium citrate, and the like.

Suspensions and emulsifiers include surfactants such as stearyl triethanolamine, sodium lauryl sulfate, lauryl aminopropionic acid, lecithin, benzalkonium chloride, benzetonium chloride, glycerin monostearate; hydrophilic polymers such as polyvinyl alcohol, polyvinyl pyrrolidone, sodium carboxymethylcellulose, methyl cellulose, hydroxymethyl cellulose, hydroxypropyl cellulose; for example, cherry cloud, carnavaro, wax, lanolin, liquid lanolin, lanolin, reduced lanolin, cyclic cellulose, ceramone, and the like. Examples include waxes such as rice wax.

Examples of the isotonic agent include sodium chloride, glycerin, and D-mannitol. Examples of the buffer include a buffer solution such as phosphate, acetate, carbonate, citrate, and the like. Examples of the analgesic include benzyl alcohol and the like. Examples of the preservative include parahydroxybenzoic acid esters, chlorobutanol, benzyl alcohol, phenethyl alcohol, dehydroacetic acid, sorbic acid, and the like. Examples of the antioxidant include sulfite, ascorbic acid, and the like.

Conventional methods can be used when the ophthalmic compositions of the present invention are in liquid form.

For liquid formulations, consideration is given to the solubility and stability of at least the antioxidant plant extract or components derived therefrom, such as crocetin or a pharmaceutically acceptable salt thereof, in water.

For example, because crocetin is water-soluble in carotenoids, which combine a water-miscible structure with an oil-miscible structure, the dosage forms of the ophthalmic compositions of the present invention may generally be aqueous or suspensions.

The dosage of the oral preparation (solid preparation, liquid preparation) of the present invention can be appropriately set according to the study disease and condition, the degree of disease, the age, body weight, and the like of the subject. The amount of crocetin is 0.075 to 75 mg/day per day, more preferably 0.1 to 25 mg/day, and more preferably 025 to 10 mg/day. The amount of extract other than crocetin is 0.1 to 5000 mg/day per day, more preferably 1 to 1000 mg/day, and more preferably 10 to 300 mg/day. The number of times of administration may be one or a plurality of times per day.

<Food>

The ophthalmic composition of the present invention may be provided in a food product. Such functional foods include health foods, functional labeling foods, health supplements, nutritional function foods, special purpose foods, specified insurance foods or ordinary foods. Since these foods contain the ophthalmic composition of the present invention, they may be suitably ingested in accordance with the respective symptoms of a person in need of prevention or treatment of myopia or ocular diseases, in particular for a growing child or young person who is susceptible to the onset and progression of myopia, especially axial myopia, and for a middle-aged and elderly person who is at increased risk of aging-related ocular diseases such as cataract, glaucoma, retinopathy, macular disease, choroidal neovascularization, posterior staphyloma and optic neuropathy. In addition to these, it can be widely ingested in expectation of an improvement effect and the like for suppression of axial extension for symptoms and diseases caused by ophthalmic axial extension.

Examples of the shape of these foods include juices, soft drinks, liquid forms such as drinks and tea, solid forms such as biscuits, tablets, granular powders, powders and capsules, pastes, jellies, soups; seasonings, semi-fluid forms such as dressings, and the like.

In particular, rice; various breads including pizza, scorn, biscuits, bagels, focachers, croissants; various noodles including buckwheat, dough, Chinese noodles, instant noodles, and cup noodles; various pastas including spaghetti, macaroni, penne, and lasania; beverages such as soft drinks, carbonated beverages, nutritional beverages, fruit drinks, lactic acid drinks, sports beverages; curry, chews, sweets such as ice cream, ice shavettes; cakes, cookies, candies, gums, chalks, chalks, chets, chests, chets, and other confectionery, sweets, chests, and other confectionery. marine and livestock processed foods such as hams and sausages; milk products such as processed milk and fermented milk; fats and oils such as salad oil, starch oil, margarine, mayonnaise, shortening, whip cream and dressing; seasonings such as sauce, dressing, miso, soy sauce and drink; soup, chew and dairy products Examples include salads, side dishes, splashes, pickles; and other various forms of health and nutritional supplements.

In addition, foods which may be provided containing the ophthalmic compositions of the present invention include supplements such as powders, granules, soft capsules, hard capsules, tablets, chewable tablets, fast disintegrating tablets, syrups, liquids, and the like.

The ophthalmic composition of the present invention can also be included in animal baits such as pets.

Any of these foods can be prepared by adding crocetin or a pharmaceutically acceptable salt thereof by methods known to those skilled in the art.

Additives are added to the food product as necessary. Such additives include, for example, glucose, fructose, sucrose, maltose, sorbitol, stevioside, rubsoside, corn syrup, lactose, mannito, dextrin, citric acid, sodium citrate, tartaric acid, malic acid, succinic acid, lactic acid, L-ascorbic acid, dl-α-tocopherol, sodium erythrosorbate, glycerin, polyglycerol fatty acid ester, sucrose fatty acid ester, sorbitan fatty acid ester, arabic gum, carrageenan, casein, gelatin, gelatin, gelatin, peptic acid, calcium, amino acid, calcium, amino acid, etc. Surfactants, dyes, perfumes, preservatives and the like may be mentioned.

The food product in the present invention may have an indication that it has a preventive effect, an ameliorative effect, or the like of myopia or ocular disease (e.g., a posterior ocular disease such as cataract, glaucoma, retinal detachment, macular hole, foveolar segregation, retinal edema, diabetic retinopathy, retinal pigment degeneration, macular edema, diabetic macular disease, myopic macular degeneration, age-related macular degeneration, myopic neuropathy, or the like). In addition, the food in the present invention may be a food with indications for use in children in the growth phase, in which the onset and progression of myopia (in particular, axial myopia) is likely to occur; for use in middle-aged and elderly patients, in whom the risk of age-related posterior ocular diseases, such as cataract, retinal detachment, glaucoma, macular degeneration, choroidal neovasculature, etc., is increased; for use in symptoms and diseases caused by axial extension; and for use in suppressing axial elongation.

As described above, the ophthalmic composition, the medicine (eye drops, oral preparations, and the like), and the food (functional food, specified health food, and the like) according to the present invention are effective for the age period in which myopia develops or progresses, in particular, for children and young people in the growth stage.

In particular, it can suppress visual acuity deterioration (onset of myopia, progression of myopia) and exerts an effect of suppressing extension of axial length, which is likely to occur mainly in children under 20 years of age and young people between 20 and 30 years of age, preferably children between 2 and 15 years of age, more preferably children between 6 and 12 years of age. It is also effective in middle-aged and older adults who are at increased risk for age-related posterior ocular diseases such as cataract, glaucoma, retinal detachment, retinopathy, maculopathy, choroidal neovascularization, posterior staphyloma, and optic neuropathy.

Ophthalmic Composition/Second Embodiment

A second embodiment of the inventive ophthalmic composition is an ophthalmic composition comprising an EGR-1 expression enhancer.

Here, the EGR-1 expression enhancing agent refers to a material capable of enhancing the expression strength of EGR-1 genes known to be involved in inhibition of ocular axial elongation.

The present ophthalmic compositions can be suitably used for the prevention or treatment of myopia and ocular diseases which are considered to be caused by axial elongation by including the EGR-1 expression enhancer.

The ophthalmic composition of the present invention has an effect of maintaining visual acuity, and is particularly effective in an age group in which myopia tends to develop and progress, such as a growing child or a young person. It is also effective against posterior ocular diseases, such as cataract, retinal detachment, glaucoma, macular degeneration, and choroidal neovascularization, which are thought to be caused by axial elongation.

Preferably, the EGR-1 expression enhancer comprises an antioxidant plant extract. As the antioxidant plant extract, a plant extract containing carotenoids and polyphenols is given as a preferable example. The carotenoids and polyphenols exemplified in the first embodiment of the present invention can be similarly exemplified here.

Of the above carotenoids, crocetin, a pharmaceutically acceptable salt of crocetin, gardenia extract, gardenia pigment, saffron extract, β-carotene, lutein, zeaxanthin, astaxanthin, marigold extract, red paplica, paplica pigment, safflower extract, apocynum extract are preferred from the standpoint of superior EGR-1 expression enhancing effect (effect of inhibiting extension of axial length), and a pharmaceutically acceptable salt of crocetin, gardenia extract, gardenia pigment, and saffron extract are more preferred, and crocetin and a pharmaceutically acceptable salt of crocetin are more preferred.

"In polyphenols, ginkgo leaf extract, mangosteen extract, strawberry seed extract, walnut polyphenol, guarana extract, java ginger extract, nobiletin, blueberry leaf extract, cassis extract, curcumin, white curcuminoid, parsley extract, japanese cypress berry extract, polymethoxyflavonoid (PMF) are preferable from the standpoint of being superior in the effect of enhancing EGR-1 expression (effect of suppressing extension of axial length), and ginkgo leaf extract, mangosteen extract, strawberry seed extract, walnut polyphenol, guarana extract, java ginger extract are more preferable, and ginkgo leaf extract is more preferable."

The content of the EGR-1 expression enhancer in the ophthalmic compositions of the present invention is not particularly limited as long as the effects of the present invention can be obtained, but is, for example, 0.001 to 20 mass %, preferably 0.01 to 10 mass %, and more preferably 0.1 to 5 mass %.

Preferred embodiments of the inventive ophthalmic compositions comprising EGR-1 expression enhancers include pharmaceuticals, foods. The description in the first embodiment can be applied to specific descriptions of other ingredients and the like which may be included in the case where the ophthalmic composition of the present invention is a medicine or a food. The part described as the antioxidant plant extract or the components derived therefrom in the first embodiment can be understood by replacing the part with the "EGR-1 expression enhancer".

Ophthalmic Composition/Third Embodiment

A third embodiment of the ophthalmic composition of the present invention is an ophthalmic composition containing an ocular axial elongation inhibitor. Here, the axial elongation inhibitor refers to a substance having an effect of suppressing the axial elongation, and the ophthalmic composition containing the substance can be suitably used for prevention or treatment of myopia or ocular disease which is considered to be one of the causes of the axial elongation. The ophthalmic composition of the present invention has an effect of maintaining visual acuity and is particularly effective in an age group in which myopia tends to develop and progress, such as a growing child or a young person. It is also effective against posterior ocular diseases, such as cataract, retinal detachment, glaucoma, macular degeneration, and choroidal neovascularization, which are thought to be caused by axial elongation.

Examples of the ocular axis elongation inhibitor include, for example, the above-mentioned EGR-1 expression enhancer, in particular, an antioxidant plant extract, preferably carotenoids, polyphenols and the like, more preferably, crocetin, a pharmaceutically acceptable salt of crocetin, ginkgo leaf extract, mangosteen extract, strawberry seed extract, walnut polyphenol, guarana extract, Java ginger extract, more preferably crocetin, a pharmaceutically acceptable salt of crocetin, and particularly preferably crocetin, a pharmaceutically acceptable salt of crocetin. The present invention also encompasses the case where an ophthalmic composition containing an axial elongation inhibitor is a medicine or a food. The description in the first embodiment can be applied to the specific description of the other components and the like. The part described as the antioxidant plant extract or a component derived therefrom in the first embodiment can be understood by replacing the "ocular axial elongation inhibitor".

<Methods for Screening Substances Effective for the Prevention or Treatment of Myopia or Ocular Diseases>

Substances useful for the prevention or treatment of myopia or ocular diseases can be screened using as an index the strength of expression of EGR-1 genes known to be involved in axial elongation. The EGR-1 gene is known to be involved in the development of the axial length, and a substance having an effect of enhancing the expression of this gene can be said to have an effect of suppressing the axial elongation.

The present screening methods include at east the steps of (1) treating cells, tissues, individuals, etc. with a test substance or a negative control substance (hereinafter also referred to as a "treatment step"), (2) measuring the expression levels of EGR-1 genes in cells or tissues, or cells or tissues of a subject (hereinafter also referred to as a "measuring step").

The test substance is preferably at least one selected from the group consisting of carotenoids, polyphenols, and pharmaceutically acceptable salts thereof. In particular, among carotenoids, crocetin and *Ginkgo biloba* extract among polyphenols are preferably used, but the present invention is not limited thereto. When two or more substances selected from the above group are used as test substances, one of them is preferably crocetin or ginkgo leaf extract. In this instance, it is preferable that the substance other than crocetin or ginkgo leaf extract is a substance that promotes an increase in EGR-1 by synergistic effects with crocetin or ginkgo leaf extract, but the present invention is not limited thereto, Specifically, the test substance can be crocetin alone or crocetin and ginkgo leaf extract.

In the case where the cells or tissues are treated with a test substance or the like in the above-mentioned treatment step, the treatment can be performed by methods well-known to those skilled in the art.

For example, the test substance or the like may be added to the culture medium of the cultured cells and cultured for a predetermined period of time, e.g., 1 to 72 hours. The subject, human or other animal, may also be ingested one or more times with a composition comprising a test substance or the like.

In the measuring step, the expression of EGR-1 genes in cells or tissues can be measured by methods well known to those skilled in the art. The expression of EGR-1mRNA in cells or tissues may be measured, for example, by quantitative RT-PCR methods. Levels of EGR-1 gene expression may also be measured by luciferase reporter gene assays according to conventional methods.

In particular, the present screening method may be said to be a screening method comprising the steps of: (a) preparing a test specimen to which is added at least one test substance selected from the group consisting of carotenoids, polyphenols, and pharmaceutically acceptable salts thereof; polyphenols, and pharmaceutically acceptable salts thereof; and (b) measuring EGR-1 expression of the test specimen (referred to as step (b)); and (c) selecting a test specimen having a EGR-1 expression effect and selecting a test substance included in the test specimen as an ophthalmic axis extension inhibitor or a EGR-1 expression enhancer (referred to as step (c)).

In step (a) above, a nucleic acid containing a reporter gene to which a EGR-1 gene is linked is introduced into a cell to be screened, and at least one test substance selected from the group consisting of carotenoids, polyphenols, and pharmaceutically acceptable salts thereof is introduced into the cell to be used as a test substance.

As the reporter gene, for example, a green fluorescent protein (GFP) gene, a luciferase gene, or the like can be used, and can be easily selected by a person skilled in the art. The nucleic acid containing the reporter gene may be any nucleic acid capable of expressing the reporter gene in a cell in which the screening method of the present invention is carried out, and may be, for example, a plasmid vector, a viral vector, or the like.

The cells used in the present screen may be any cell in which the EGR-1 gene is functional and the reporter gene is expressible, or may be derived from any species. For example, mammalian cells (mouse, rat, human, etc.) or avian cells (chick, etc.) may be used.

Here, as the study substance to be added to the test article, the test article may be prepared by serially diluting the concentration thereof to prepare a test article containing a plurality of concentrations of the test article. Control experiments containing negative control substances can also be prepared in the same manner as the test bodies, except that they contain negative control substances.

Using the test specimen thus prepared, the test specimen is subjected to the following step (b).

The step (b) is a step of measuring the EGR-1 expression of the test specimen. For example, the step of measuring the EGR-1 expression by expression of the reporter genes. In this case, a change in the expression of the reporter gene can be easily detected and measured by a person skilled in the art. For example, in the case where a gene of a luminescent protein such as GFP or luciferase is used as a reporter gene, after culturing the cells, the lysate may be transferred to a plate suitable for measuring luminescence and the luminescence may be measured, or the luminescence from the cultured cells may be directly measured. As an instrument used for the measurement, for example, a known luminometer or the like can be used.

In the step (c) above, in order to select a substance having a strong action of inhibiting axial elongation or EGR-1 expression, a test specimen having an EGR-1 expression level measured in the step (b) above which is larger than that of a control experiment may be selected. That is, when a gene of a luminescent protein is used as a reporter gene, a test specimen having a large luminescence amount may be selected.

The ocular axial elongation inhibitor or the EGR-1 expression enhancer obtained by the present screening methods can be formulated in ophthalmic compositions, functional foods, and the like for the purpose of improving the axial elongation inhibitory effect or the EGR-1 increasing effect, or for the purpose of effectively improving myopia or ocular diseases.

EXAMPLES

The present invention is explained in more detail by Examples and Comparative Examples.

Experiment 1

<Preparation of Stable Expression Strains>

Confirmation experiments of EGR-1 inductive effects were carried out. First, a human fetal kidney cell line (HEK293T) and a lentiviral vector (trade name "Cignal Lenti EGR-1 Reporter", Quiagen) into which an EGR-1 gene has been introduced were prepared. On Day 1, human fetal kidney cell lines were seeded in 24 well plates and grown in a 5% $CO_2$ incubator at 37° C., for 24 hours. On day 2, 150 µL/well of lentivirus was transduced and an additional 12 µL of SureENTRY transduction reagents (Quiagen) were added and placed in a 5% C©2 incubator at 37° C. overnight. The lentiviruses were then removed with Medium (vehicle) and selected using puromycin (1 µg/mL). Through these procedures, a HEK293T cell line (stable expression cell line) was prepared by transfecting EGR-1 activity-dependent Firefly-Luciferase.

<Analysis of Gene Expression>

Next, gene expression analysis using luciferase was performed. A multimode plate reader (Synergy HTX, Inc., BioTek) was used for the analysis. EGR-1 activity dependent-HEK293T cell-lines transgenic for Firefly-Luciferase were seeded at $1 \times 10^4$ per well in 96 well plates. After the cells were inseminated to the bottom of the plates, test reagents were added, and the intensity of emission was measured 24 hours later using a Luciferase assay system made by Promega.

Test reagents include crocetin (Crovit P, manufactured by RIKEN VITAMIN CO., LTD.), Ginkgo leaf extract (manufactured by Indena Japan CO., LTD.), Walnut polyphenol (manufactured by Oliza Polyphenol-P10), Mangosteen extract (manufactured by Mangostin Aqua Co., Ltd.), Strawberry seed extract (manufactured by Oliza Oil Co., Ltd.), Guarana extract (manufactured by Galana Expander, manufactured by Japan Powder Co., Ltd.), Java ginger extract (manufactured by Hosoda SHC Co., Ltd.), PMA (a positive control for EGR-1 expression, 12-myristate 13-acetate, manufactured by abcam Corporation) was also used. The above test reagents were dissolved in DMSO (dimethylsulfoxide) to final concentrations of 0.25 mg/mL, left overnight at ambient temperature (about 20° C.), and then centrifuged to add the supernatant to the cell culture medium to obtain 0.25 mg/mL test reagents.

In the test in which the concentration was changed, a Crovit P was used. Crovit P was a powder with a content of more than 75% of crocetin, and the Crovit P was dissolved in DMSO (dimethylsulfoxide) so as to be 100 mg/mL, and left at room temperature (about 20° C.) overnight. The supernatant was then added to the cell culture medium by centrifugation to obtain 0.125 mg/mL test reagent and 0.25 mg/mL test reagent.

<Result>

Figure 2:
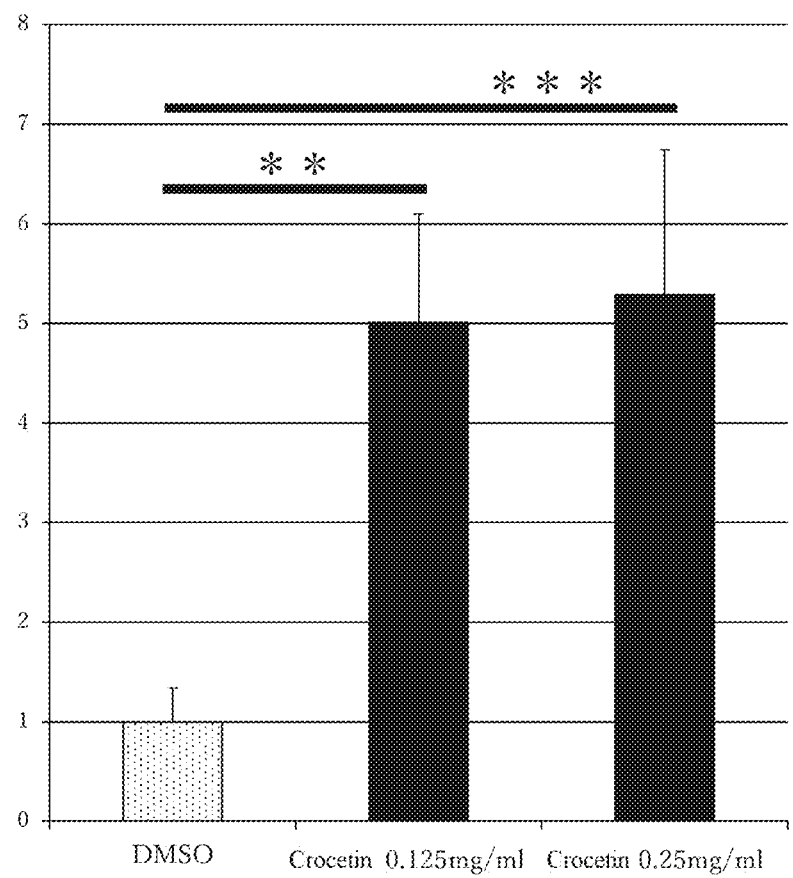
FIG. 2 is a graphical representation of the effects of varying the content of test reagents included in the inventive ophthalmic compositions on EGR-1 gene expression.

FIG. 1 is a graphical representation of the results of inducing EGR-1 expression with and without the various test reagents described above. FIG. 2 is a graph showing the results when the concentration of crocetin (Crovit P) used as the test reagent is changed. As can be seen from FIG. 1, when 0.25 mg/mL of crocetin (Crovit P) was added, the luminescence intensity was 5.7-fold, which was remarkably different from that of the positive control PMA, as compared with the case where only DMSO containing no test reagents was added. That is, the remarkable EGR-1 inducing effects of crocetin were confirmed. In addition, it was confirmed that the luminescence intensity of *Ginkgo biloba* extract was about 3.8 times, and the luminescence intensity of other test reagents was equivalent to that of PMA as a positive control.

As can be seen from FIG. 2, the results obtained when 0.125 mg/mL of Crovit P was added and the results obtained when 0.25 mg/mL of Crovit P was added were remarkably enhanced compared to the results obtained when only DMSO containing no test reagents was added. In other words, the Dunnett test with DMSO was highly significant at 0.125 mg/mL for 5.0-fold ($P<0.01$) and at 0.25 mg/mL for 5.2-fold ($P<0.005$), respectively, and EGR-1 expression was markedly enhanced by crocetin in the in vitro.

Non-Patent Documents 9 and 10 are research papers that report the relation between EGR-1 inducing effects and ocular axial length, and it has been verified that axial elongation is observed in mice knocked out of EGR-1 (Non-Patent Document 9) and that EGR-1 expression is enhanced by artificially suppressing ocular axial elongation (Non-Patent Document 10). However, whether agents capable of enhancing EGR-1 expression at the cellular level inhibit axial elongation at the individual level, and consequently inhibit myopia progression, has not yet been tested.

Then, a validation test of axial elongation in myopic model animals was carried out.

Experiment 2

In Experiment 2, a validation test of ocular axial elongation in myopia model animals was performed. C57BL/6J mice, 3 weeks old, were used. In the light environment (12 hours/12 hours), the control feed group (MF, Oriental Yeast Co., Ltd.) or the 0.003% Crovit P mixed feed (Oriental Yeast Co., Ltd.) was continuously given from 3 weeks to 6 weeks.

<Measuring Equipment, Measuring Procedure>

Spectral domain optical coherence tomography (Envisu R4310, manufactured by Leica Corporation), infra-red photorefractor for mice (Infrared photorefractor for mice), Version 1. 0.15b3, manufactured by Horiuchi Electric Co., Ltd. were used as measuring apparatuses. Incidentally, the infra-red photorefractor for mouse is an improved device which can recognize the eyes of a mouse manufactured by Prof. F. Schaeffel (Steinbeis Transfer Center and Germany), and is a device which illuminates the eyes of the mouse using infrared LEDs, and at the same time, detects infrared reflected light from the eyes using infrared cameras, and judges myopia from the shapes and intensities of the reflected light. This device is widely used in myopia research areas, and it is also possible to compare data across laboratories. For refraction, a value obtained by averaging 100 times after a stable value was obtained was adopted. For each group, welch-t tests were performed and P-values of 0.05 or less were considered significant ("*") in the graph, and P-values of 0.01 or less were considered highly significant ("*") in the graph.

As a test reagent, midrin P (registered trademark, Santen Pharmaceutical Co., Ltd.) was used to stabilize the pupil at the time of measurement. In addition, three types of mixed anesthesia (medetomidine hydrochloride (domitol/registered trademark, All Japan Pharmaceutical Industry Co., Ltd.), mitazolam (Dormicum/registered trademark, Astellas Pharma Corporation), butorphanol tartrate (Betlefar/registered trademark, Meiji Seika Corporation)), tipamezole hydrochloride (antisedan/registered trademark, All Japan Pharmaceutical Industry Co., Ltd.), and sodium pentobarbital (somnopentyl/registered trademark, Kyoritsu Pharmaceutical Co., Ltd.) were used to awake anesthesia.

The test initially measured ocular parameters. This measurement was (1) binocular mydriasis by instillation of Midrin P®, (2) anesthetized by intraperitoneal administration of triple anesthesia, (3) refraction was measured by an infrared photorefractor for mice, and (4) axial length was measured by spectral domain optical coherence tomography.

Mice were then fitted with spectacles. Specifically, the top skin was excised with a scissors, and a dental superbond (4-META/MMA-TBB resin) was attached to the skull with a spectacle post made with a 3 D printer, and the left eye was fitted with a 0 Diopter lens and the right eye with a −30 Diopter lens.

Then, (a) he took an anti-sedan (registered trademark) from the anesthetic, (b) he nurtured each feed group (when the eyeglass lenses were soiled, he cleaned them as needed), and (c) he again measured the eye parameters mentioned above when six weeks of age.

<Result>

Figure 3:
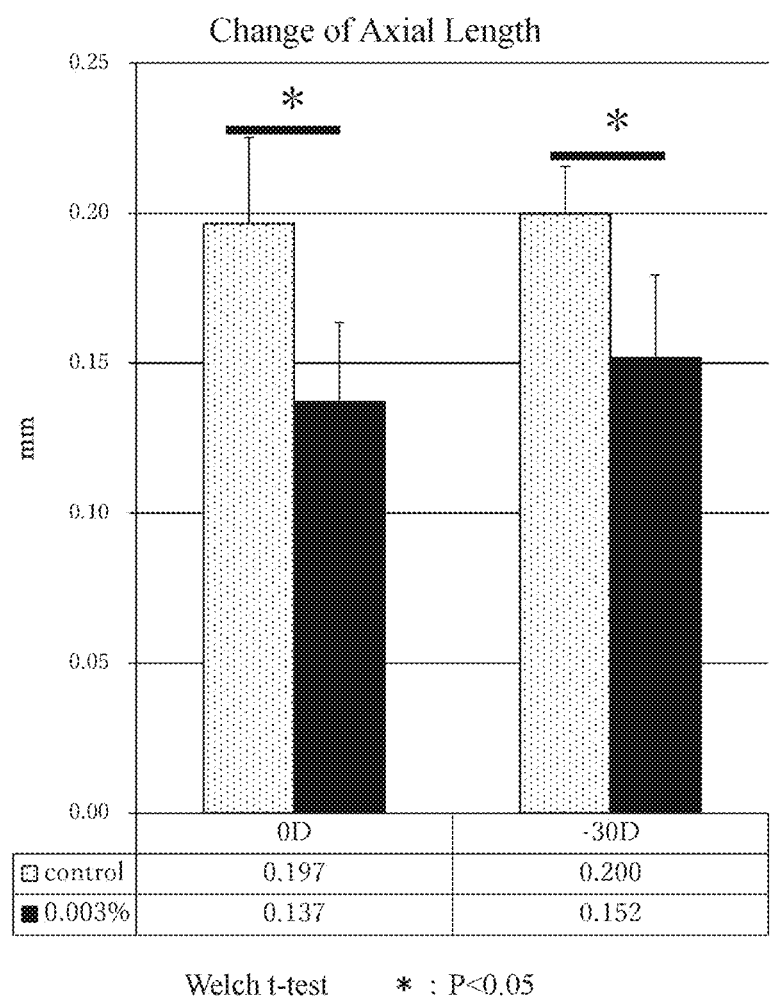
FIG. 3 shows the results of the axial length measurement obtained in Experiment 2.
Figure 4:
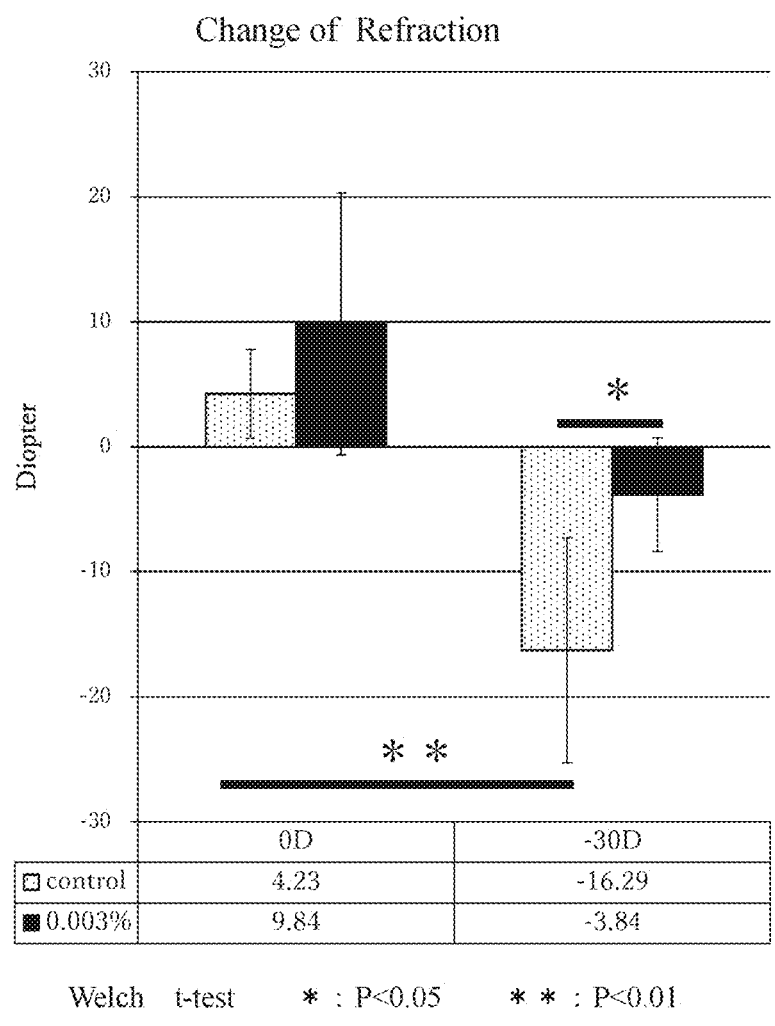
FIG. 4 shows the results of refraction measurements obtained in Experiment 2.

FIG. 3 is a result of the axial length measurement, and FIG. 4 is a result of the refraction measurement. From the results shown in FIG. 3, in myopia-induced mice (0.003% in the graph) fed a mixed diet of 0.003% of Crovit P whose EGR-1 expression enhancing effect was confirmed in in vitro [Experiment 1], axial elongation was significantly suppressed (p<0.05) compared with mice fed the control diet (control in the graph). The results in FIG. 4 also showed that myopia induction (control of −30D in the graph) significantly reduced refraction (Diopter) and induced significant myopia in mice (P<0.01) compared to mice without myopia induction (control of OD in the graph). Also, in myopia-induced mice (0.003% of −30D in the graph) similarly fed the Crovit P diet, refraction was significantly (P<0.05) higher than in mice fed the control diet (control of −30D in the graph), and myopia induction was markedly suppressed by crocetin. Thus, crocetin significantly prevented myopic progression in the in vivo. In addition, it was confirmed that the ocular axial elongation inhibitory components in the actual organism can be efficiently screened by screening the drug having the EGR-1 expression enhancing effect with in vitro,

What is claimed is:

1. A method for treating axial myopia in a human in need thereof, comprising administering a therapeutically effective amount of crocetin to the human to effectively treat the axial myopia wherein the therapeutically effective amount is 0.075 to 75 mg/day.

2. The method of claim 1, wherein the method further comprises administering to the human in need thereof a therapeutically effective amount of carotenoids or polyphenols other than ginkgo leaf extract.

3. The method of claim 1, wherein the therapeutically effective amount of crocetin is administered to children during growth.

4. The method of claim 1, wherein the axial myopia is high myopia.

5. The method of claim 1, wherein the therapeutically effective amount of crocetin inhibits ocular axial elongation.

6. The method of claim 1, wherein the therapeutically effective amount of crocetin enhances EGR-1 expression.

7. The method of claim 1, wherein the human is a near worker or an indoor worker.

* * * * *